US010156549B2

(12) United States Patent
Molenaar et al.

(10) Patent No.: US 10,156,549 B2
(45) Date of Patent: *Dec. 18, 2018

(54) METHOD AND SYSTEM FOR EXAMINING THE INTERIOR MATERIAL OF AN OBJECT, SUCH AS A PIPELINE OR A HUMAN BODY, FROM A SURFACE OF THE OBJECT USING ULTRASOUND

(71) Applicant: Rontgen Technische Dienst B.V., Rotterdam (NL)

(72) Inventors: Marcel Meijlom Molenaar, Rotterdam (NL); Steven Ferdinand Kleijer, Rotterdam (NL)

(73) Assignee: RONTGEN TECHNISCHE DIENST B.V., Rotterdam (NL)

( * ) Notice: Subject to any disclaimer, the term of this patent is extended or adjusted under 35 U.S.C. 154(b) by 214 days.

This patent is subject to a terminal disclaimer.

(21) Appl. No.: 14/991,013

(22) Filed: Jan. 8, 2016

(65) Prior Publication Data
US 2016/0334372 A1 Nov. 17, 2016

Related U.S. Application Data

(62) Division of application No. 13/603,748, filed on Sep. 5, 2012, now Pat. No. 9,261,487.

(30) Foreign Application Priority Data

Sep. 5, 2011 (NL) .................................... 2007348

(51) Int. Cl.
G01S 15/00 (2006.01)
G01N 29/06 (2006.01)
(Continued)

(52) U.S. Cl.
CPC ............. *G01N 29/069* (2013.01); *A61B 8/00* (2013.01); *A61B 8/5207* (2013.01);
(Continued)

(58) Field of Classification Search
USPC .......................................................... 367/11
See application file for complete search history.

(56) References Cited

U.S. PATENT DOCUMENTS 4,170,142 A 10/1979 Davis
5,469,851 A 11/1995 Lipschutz
(Continued)

FOREIGN PATENT DOCUMENTS

EP 2182352 A2 5/2010

OTHER PUBLICATIONS

Australian Government, Patent Examination Report No. 1 in corresponding Australian Patent Application No. 2015238867 dated Jul. 23, 2016 (2 pages).
(Continued)

*Primary Examiner* — James R Hulka
(74) *Attorney, Agent, or Firm* — Leydig, Voit & Mayer, Ltd.

(57) ABSTRACT

A method and system are described for examining the interior material of an object from a surface of an object using ultrasound having a frequency of at least 100 kHz. The method comprises the step of transmitting at least a first ultrasound signal by a first ultrasound transmitter of a first number of ultrasound transmitters to the interior material of the object for forming a first image in order to determine, according for example to the principle of inverse wave field extrapolation, where in the interior material of the object reflections and/or diffractions occur. Reflections and/or diffractions of the first ultrasound signal from the interior material of the object are received using a second number of
(Continued)

ultrasound receivers which are acoustically coupled to the surface of the object at positions which are distributed in at least one dimension of the surface of the object. With each of the second number of ultrasound receivers, a receiving signal is generated from the received reflections and/or diffractions of the first ultrasound signal from the interior material of the object, and each of the receiving signals generated by one of the ultrasound receivers is processed separately into a separate dataset. The separate datasets of all the ultrasound receivers are combined to the first image.

42 Claims, 1 Drawing Sheet

(51) Int. Cl.
| | |
|---|---|
| *G03B 42/06* | (2006.01) |
| *G01S 15/89* | (2006.01) |
| *A61B 8/00* | (2006.01) |
| *G01N 29/26* | (2006.01) |
| *G01N 29/36* | (2006.01) |
| *G01N 29/44* | (2006.01) |
| *G01N 29/52* | (2006.01) |
| *A61B 8/08* | (2006.01) |

(52) U.S. Cl.
CPC ........... *G01N 29/262* (2013.01); *G01N 29/36* (2013.01); *G01N 29/4472* (2013.01); *G01N 29/52* (2013.01); *G01S 15/8915* (2013.01); *G03B 42/06* (2013.01); *G01N 2291/106* (2013.01)

(56) References Cited

U.S. PATENT DOCUMENTS

| | | | |
|---|---|---|---|
| 5,588,032 A | 12/1996 | Johnson et al. | |
| 5,766,129 A | 6/1998 | Mochizuki | |
| 5,911,691 A | 6/1999 | Mochizuki et al. | |
| 7,570,742 B2 | 8/2009 | Johnson et al. | |
| 7,650,789 B2 | 1/2010 | Portzgen et al. | |
| 9,261,487 B2 * | 2/2016 | Molenaar | G01N 29/069 |
| 2003/0187357 A1 | 10/2003 | Richard | |
| 2004/0034307 A1 * | 2/2004 | Johnson | A61B 5/05 |
| | | | 600/459 |
| 2006/0122506 A1 | 6/2006 | Davies | |
| 2006/0184038 A1 | 8/2006 | Smith et al. | |
| 2007/0277611 A1 * | 12/2007 | Portzgen | G01N 29/07 |
| | | | 73/592 |
| 2009/0034756 A1 | 2/2009 | Volker et al. | |
| 2013/0058191 A1 * | 3/2013 | Molenaar | G01N 29/069 |
| | | | 367/11 |

OTHER PUBLICATIONS

European Patent Office, Examination Report in corresponding European Patent Application No. 12183138.2, dated Sep. 7, 2016 (7 pages).
Niels Portzgen et al., "Inverse Wave Field Extrapolation: A Different NDI Approach to Imaging Defects," IEEE Transactions on Ultrasonics, Ferroelectrics, and Frequency Control, vol. 54, No. 1, pp. 118-127 (Jan. 2007).
N. Portzgen et al., "Advances in Imaging of NDT Results," WCNDT, Aug. 30, 2004 (8 pages).

* cited by examiner

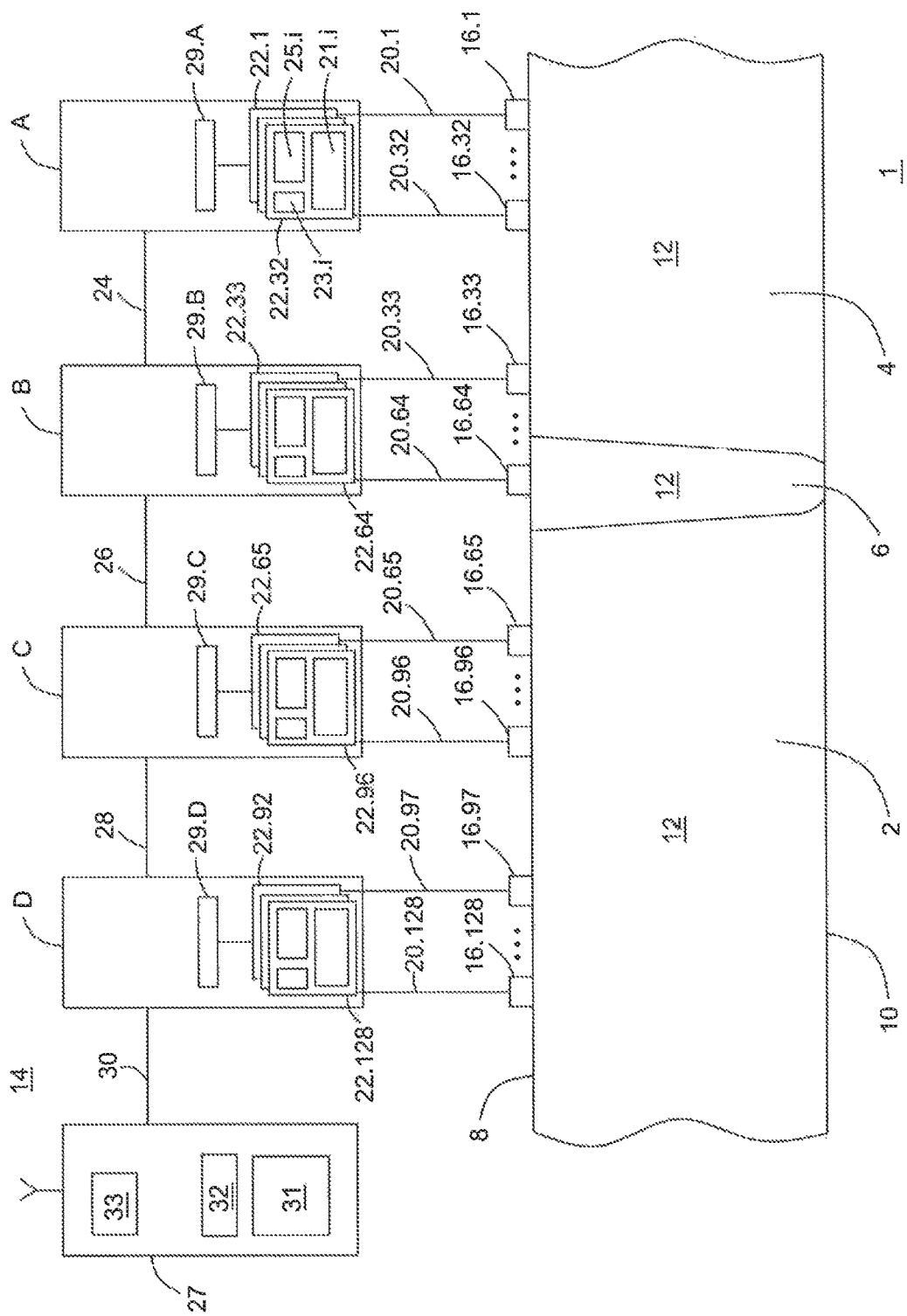

METHOD AND SYSTEM FOR EXAMINING THE INTERIOR MATERIAL OF AN OBJECT, SUCH AS A PIPELINE OR A HUMAN BODY, FROM A SURFACE OF THE OBJECT USING ULTRASOUND

CROSS-REFERENCE TO RELATED APPLICATIONS

This application is a divisional application of U.S. application Ser. No. 13/603,748, filed Sep. 5, 2012 which claims priority to The Netherlands Application No. 2007348, filed Sep. 5, 2011, which are both expressly incorporated by reference in their entirety, including any references contained therein.

The invention relates to a method for examining the interior material of an object according to the preamble of claim 1.

Such a method is known from U.S. Pat. No. 7,650,789. In this known method the receiving signals are processed in combination in order to determine, according to the principle of inverse wave extrapolation, where in the interior material of the object reflections and/or diffractions occur. Typically such a method uses 16, 32 or even up to 1024 ultrasound receivers. In order to perform examination of the interior material of an object in the known method each receiving signal is sent to a processing means in which all the receiving signals are processed in combination. Although the known method is efficient in case relatively small numbers of ultrasound receivers are used, a bottle neck is created in the transmission of the receiving signals to the processing means in case a larger number of ultrasound receivers is used. In case more ultrasound receivers are used more data have to be transferred to the processing means, thereby reducing inspection speed and making it very difficult to perform a real time inspection.

It is an object of the invention to provide a method for examining the interior material of an object in which a large number of ultrasound receivers can be used without reducing inspection speed. It is a further object of the invention to provide a method for examining the interior material of an object which enables real time inspection with larger numbers of ultrasound receivers. It is a further object of the invention to provide a method for examining the interior material of an object in which the number of ultrasound receivers used can easily be enlarged without reducing processing speed and/or processing performance.

To realize at least one of these objects or at least a part of one of these objects, the method as described in the preamble is in accordance with the invention characterized in that each of the receiving signals generated by one of the ultrasound receivers is processed separately, and wherein the separately processed receiving signals of a plurality of, preferably all, the ultrasound receivers are combined to the first image. Since each receiving signal is processed separately the size of data to be transferred is strongly reduced whereby inspection speed can be maintained high. In addition the processing speed is independent on the number of receiving signals to be processed (i.e. independent on the number of ultrasound receivers used) since each receiving signal is processed separately, whereby processing speed can be maintained high and the number of ultrasound receivers used can virtually limitlessly be extended. Although in the method known from U.S. Pat. No. 7,650,789 the receiving signals are processed according to the principle of inverse wave extrapolation, the present invention is also applicable to other processing techniques. Please note that although the term (first) image is used, this does not necessarily mean that this image is a picture. In the context of this application image refers to a combination of separately processed receiving signals. The separately processed receiving signals may comprise datasets. As discussed below a dataset may be in the form of a data point, a picture, a picture element or pixel or a pixel value.

In an embodiment of a method according to the invention the separate processing of each receiving signal comprises converting the receiving signal into a separate dataset in a certain data format; and using this separate dataset in forming the first image. In this way it is, by properly choosing the data format possible to perform easy, fast and accurate addition of datasets, thereby reducing or even removing temporary storage.

In an embodiment of a method according to the invention each of the separate datasets is temporarily stored at least until the separate datasets of said plurality of the second number of ultrasound receivers have been obtained, after which all the separate datasets are combined to the first image, which first image is at least temporarily stored. Preferably, after the first image has been stored all stored separate datasets are deleted, so that the ultrasound receivers are ready to generate further receiving signals without needing large storage capacity and thereby preventing reduction of communication and processing speed.

In an alternative embodiment of a method according to the invention the method comprises:

a) processing one of the receiving signals generated by one of the ultrasound receivers into a separate dataset, and storing said separate dataset at least temporarily in a memory, b) processing another one of the receiving signals generated by another one of the ultrasound receivers, different from said one of the ultrasound receivers, separately into a another separate dataset, combining said another separate dataset with the stored separate dataset into a combined dataset, and replacing said stored separate dataset in said memory by said combined dataset, c) processing a further one of the receiving signals generated by a further one of the ultrasound receivers, different from the ultrasound receivers of which the receiving signals have already been processed, separately into a further separate dataset, combining said further separate dataset with the stored combined dataset into a further combined dataset, and replacing said stored combined dataset in said memory by said further combined dataset, and d) repeating step c) until the receiving signals generated by said plurality of the second number of ultrasound receivers are processed, and wherein the combined dataset of said plurality of the second number of ultrasound receivers is the first image which is at least temporarily stored. By thus combining one dataset with another dataset to a combined dataset and combining a dataset with a combined dataset until all the datasets are combined to the first image an increase in processing speed can be obtained.

A further increase in processing speed can be realized in a preferred embodiment of a method according to the invention when the receiving signals generated by two or more of ultrasound receivers are separately processed in parallel, said parallel processing optionally being performed without storing datasets. Preferably all the separate datasets are made available in a synchronized way (to reduce or even completely remove temporary storage of the datasets), after which all the separate datasets obtained are combined to the first image, which first image is at least temporarily stored.

In a further alternative embodiment of a method according to the invention the second number of ultrasound receivers is composed of individual groups of ultrasound receivers, each individual group containing a third number of ultrasound receivers, the second number divided by the third number preferably being an integer, wherein the separate datasets of all the ultrasound receivers of one group of ultrasound receivers are combined to a sub-image, and the receiving signals generated by all the ultrasound receivers of one group being separately processed in parallel. Please note that although the term sub-image is used, this does not necessarily mean that this sub-image is a picture. In the context of this application sub-image refers to a combination of separate datasets. In this way a very efficient method for examining the interior material of an object is realized in which per third number of ultrasound receivers a sub-image can be generated in a fast manner and in which the method can easily be adapted to an extension of the number of ultrasound receivers by adding a third number of ultrasound receivers to the already present number of ultrasound receivers. Preferably, each of the sub-images is temporarily stored in a memory at least until it is further processed. In a first aspect of this further alternative embodiment the number of groups is three of more, and a sub-image is combined with another sub-image to a combined sub-image, said combined sub-image being temporarily stored in a memory at least until it is further processed by combining said combined sub-image with a further sub-image, different from already processed sub-images, and wherein the combination of all sub-images is the first image which first image is at least temporarily stored. In a second aspect of this further alternative embodiment each of the sub-images is temporarily stored at least until the sub-images of all the groups have been obtained, after which all the sub-images are combined to the first image, which first image is temporarily stored. In the latter case it is advantageous that after the first image has been stored the sub-images are deleted.

In an embodiment of a method according to the invention the second number of ultrasound receivers is distributed in an array extending in one dimension of the surface of the object, and the method preferably comprises the step of moving the array, preferably sideways with regard to the extension of the array, for enabling the construction of a three dimensional first image. In this case the ultrasound receivers are arranged relative to each other according to a unidimensional array, and this unidimensional array can be moved along the surface of the object in a known manner for obtaining receiving signals coming from the ultrasound receivers distributed in two dimensions over the surface. By moving the unidimensional array along the surface, receiving signals can still be obtained which come from ultrasound receivers distributed in two dimensions over the surface of the object to obtain a three-dimensional image.

In a further embodiment of a method according to the invention the ultrasound receivers are arranged relative to each other according to a two- or three dimensional array. In that case, the ultrasound receivers do not necessarily need to be moved for obtaining a three-dimensional image.

In an advantageous embodiment of a method according to the invention the method comprises the further step of transmitting at least a further ultrasound signal by a further ultrasound transmitter of said first number of ultrasounds transmitters to the interior material of the object for forming a further image in the same way as the first image, according to for example the principle of inverse wave field extrapolation, said further ultrasound transmitter being different from the first ultrasound transmitter. By using more ultrasound signals coming from other ultrasound transmitters it is possible to more accurately define the location and orientation of a defect in the interior material of the object where reflections and/or diffractions occur. In an embodiment of a method according to the invention the first ultrasound signal and at least one further ultrasound signal are transmitted simultaneously. In using last manner it is possible that the first ultrasound signal is transmitted by a first group of ultrasound transmitters and a further ultrasound signal is simultaneously (or in another embodiment consecutively) transmitted by a further group of ultrasound transmitters, said first and further group of ultrasound transmitters being at least partially composed of different ultrasound transmitters.

In a first aspect of this advantageous embodiment enabling increased processing speed the first and the further image are combined and the combined image is stored in the memory. Preferably after the combined image has been stored in the memory, the first and/or the further image are deleted. Optionally the combined image of the images originating from all the ultrasound transmitters of the first number of ultrasound transmitters is transmitted for further processing.

In a second aspect of this advantageous embodiment the first and further images are transmitted separately for further processing.

In a third aspect of this advantageous embodiment providing even more increased processing speed a sub-image originating from the further ultrasound signal is combined with the first image to a combined hybrid image, said combined hybrid image being temporarily stored in a memory at least until it is further processed by combining said combined hybrid image with a further sub-image originating from the further ultrasound signal, different from an already processed sub-image originating from the further ultrasound signal, and wherein the combination of all sub-images originating from the further ultrasound signal with the first image is at least temporarily stored.

In an embodiment of a method according to the invention the ultrasound transmitters also form the ultrasound receivers, the first number being equal to the second number. In this way the number of elements necessary to execute the method can be reduced thereby providing a compact system to perform the method. Alternatively the ultrasound transmitters are separate from the ultrasound receivers.

In an advantageous embodiment of a method according to the invention the receiving signals are processed in real time. Preferably the method according to the invention is used to examine a weld of a metal, plastic or composite pipeline or a wall of a metal, plastic or composite pipeline or a human body.

In a preferred embodiment of a method according to the invention a dataset is in the form of a data point, a picture, a picture element or pixel or a pixel value. Preferably the data format is chosen such that addition of datasets is facilitated. In dependency of the processing system used and the computational capacity thereof the inspection speed can be maintained at a desired level when the separate processing of each receiving signal yields a dataset in the form of a data point, a picture, a picture element or pixel or a pixel value. In particular useful for most of the processing system is when the processing digitizes the receiving signals in pixel values and in which these pixel values are at least temporarily buffered.

The invention also relates to a system for examining the interior material of an object from a surface of an object using ultrasound having a frequency of at least 100 kHz, wherein the system is provided with at least a first ultrasound transmitter of a first number of ultrasound transmitters for supplying ultrasound to the interior material of the object, a second number of ultrasound receivers which are acoustically coupled to the surface of the object at positions which are distributed in at least one dimension of the surface of the object, for receiving reflections and/or diffractions of the ultrasound from the interior material of the object, and signal-processing means for processing receiving signals coming from the respective ultrasound receivers, wherein, during use, a receiving signal is generated with each of the ultrasound receivers, wherein the signal-processing means are arranged to process receiving signals coming from the ultrasound receivers into a first image according to for example the principle of inverse wave extrapolation in order to determine where in the interior material of the object reflections and/or diffractions of the ultrasound occur, characterized in that the signal-processing means are arranged for processing receiving signals coming from the ultrasound receivers separately, and for combining the separately processed receiving signals of a plurality of, preferably all, the ultrasound receivers to the first image. The separately processed receiving signals may comprise datasets. As discussed below a dataset may be in the form of a data point, a picture, a picture element or pixel or a pixel value.

In a preferred embodiment of the system in accordance with the invention the signal-processing means are arranged for during processing of each receiving signal converting the receiving signal into a separate dataset in a certain data format, and using this separate dataset in forming the first image.

In an embodiment of a system according to the invention the signal-processing means comprises a number of signal-processing units, said number being equal to the second number, each signal-processing unit comprising an acquisition means for acquiring a receiving signal coming from a respective ultrasound receiver, a processing means for processing said receiving signal from the respective ultrasound receiver and an optional memory for at least temporarily storing a respective receiving separate dataset. Preferably each processing unit digitizes each receiving signal into a pixel value and preferably buffers this pixel value at least temporarily.

In a particular embodiment of a system according to the invention the second number of ultrasound receivers is composed of individual groups of ultrasound receivers, each individual group containing a third number of ultrasound receivers, the second number divided by the third number preferably being an integer, wherein the signal-processing units associated with the ultrasound receivers of each one group of ultrasound receivers are combined into a modular unit, the signal-processing units of a modular unit being arranged for combining the separate datasets of all the ultrasound receivers of one group of ultrasound receivers to a sub-image. In this way the system can easily be adapted to the use of additional ultrasound receivers by adding another modular unit to the already existing modular units while maintaining processing and communication speed.

Further and/or alternative embodiments of a system according to the invention are defined in the dependent claims.

The invention will now be further explained with reference to an example thereof represented in the drawing, in which:

FIG. 1 shows a schematic cross section in axial direction of two parts of a pipeline connected to each other by means of a weld and an embodiment of a system according to the invention for carrying out a method according to the invention.

In FIG. 1, reference numeral 1 designates an object comprising a first pipeline 2 and a second pipeline 4 and a circumferential weld 6 with which the first pipeline 2 and the second pipeline 4 are connected with each other. Each pipeline is provided with an outer surface 8 and an inner surface 10 between which interior material 12 is present. The circumferential weld 6 is likewise provided with interior material 12. The pipeline may be of metal, plastic or a composite material.

FIG. 1 further shows a system 14 for examining, from a surface of an object, in this example from the outer surface 8 of the pipelines 2, 4 and an outer surface 8 of the weld 6, the interior material 12 of the object 1, particularly that part of the object that comprises the weld 6.

The system 14 is in this example provided with a 128 ultrasound receivers $16.i$ ($i=1, 2, 3, \ldots, 128$) of which only the receivers 16.1, 16.32, 16.33, 16.64, 16.65, 16.96, 16.97 and 16.128 are shown, and which are arranged relative to each other according to a unidimensional array. In the shown embodiment the ultrasound receivers are divided into individual groups each containing exactly the same number of ultrasound receivers in this case 32, such that in the shown embodiment there are four groups of 32 ultrasound receivers each. Please note that in alternative embodiments, not shown, the number of ultrasound receivers can be different from 128, and can in fact be any desirable natural number. In addition the number of ultrasound receivers forming one individual group of ultrasound receivers can also be any desired number including the case that one receiver forms one group or all receivers form one group.

The unidimensional array extends in axial direction of the pipelines 2, 4. The system is further provided with a first number of ultrasound transmitters for supplying ultrasound to the interior material 12 to be examined. In this example, each ultrasound receiver $16.i$ is also designed as an ultrasound transmitter $16.i$, and is herein also referred to as ultrasound receiver $16.i$. In an alternative embodiment, the ultrasound transmitters and ultrasound receivers are separate from each other.

Each ultrasound receiver element $16.i$ is connected with its own signal-processing unit $22.i$ via a respective line $20.i$, only a few of which are indicated in FIG. 1. The system 14 is further provided with transport means (not shown) known per se, to move the unidimensional array of ultrasound transmitter and receiver elements in radial direction around the object. Each signal-processing unit $22.i$ comprises an acquisition means $21.i$ for acquiring a receiving signal coming from the respective ultrasound receiver $16.i$, a processing means $23.i$ for separately processing said receiving signal from the respective ultrasound receiver $16.i$. In the present example the processing unit digitizes the receiving signal and processes it into a separate pixel value, and optionally comprises a memory $25.i$ for at least temporarily storing or buffering a respective separate pixel value. Please note that in different embodiments of the invention the processing unit may separately process the receiving signals into a dataset different from a pixel value having a digital format. Such a dataset may be in the form of a data point, a picture or a picture element (pixel), and may be in a different data format, such as for example a hexadecimal format. The present embodiment will however, be described with reference to a pixel value as a dataset.

The signal-processing units 22.*i* associated with the ultrasound receivers 16.*i* belonging to one group of ultrasound receivers are thus combined into a modular unit A, B, C, D, in the embodiment shown in FIG. 1 there thus are four modular units.

The operation of the system is as follows. Activating, for instance, a first one of the ultrasound transmitter and receiver elements 16.*i*, a first ultrasound signal is supplied to the interior material 12 of the object 1 in a pulsed manner. Simultaneously or thereafter a second and a further one of the ultrasound transmitters are activated for supplying a second and further ultrasound signal to the interior material. For this purpose, the ultrasound transmitter and receiver elements are acoustically coupled to the interior material. In practice, this can for example be realized by applying a liquid film to the outer surface of the object, while the ultrasound transmitter and receiver elements are placed so as to abut the surface of the object 1. Alternatively a wedge can be used to couple the transmitter and receiver elements to the surface of the object. The ultrasound supplied has a frequency higher than 100 kHz. The transmission of the ultrasound is controlled by a communication and control unit 27, which together with the signal-processing units 22.*i* form the processing means of the system, such that, in this example, the ultrasound transmitter and receiver elements 16.*i* transmit simultaneously at a pulse repeat frequency which is, for instance, higher than 25 Hz. In an alternative embodiment the transmission can be performed consecutively. The ultrasound will propagate through the material of the object 1 and reflection and/or diffraction will occur when the sound passes or hits a transition in the material (such as walls and/or welding flaws). Such a reflection and/or diffraction can be taken as a new virtual source whose sound energy in turn propagates through the material.

With the unidimensional array of ultrasound transmitter and receiver elements 16.*i*, the ultrasound coming from the "new virtual sources" is in turn received. Each virtual source consists of a collection of point sources whose positions can be determined. Therewith, the position, magnitude and shape of the respective virtual source can also be determined. Thus, each ultrasound receiver 16.*i* generates a receiving signal which is acquired by the acquisition means 21.*i* of its respective signal-processing unit 22.*i*. In each signal-processing unit the respective receiving signal is processed separately from the other receiving signals in the other signal-processing units into a separate pixel value. Each separate pixel value is at least temporarily stored in the memory 25.*i* of its respective signal-processing unit 22.*i*. Alternatively, each of the separate datasets can be made available in a synchronized way by e.g. parallel processing (to reduce or even completely remove temporary storage of the datasets), after which a plurality of, preferably all, the separate datasets are combined to the first image, which first image is at least temporarily stored.

The receiving signals coming from the receivers are thus processed separately in order to determine, according to for example the principle of the inverse wave field extrapolation, where in the interior material 12 of the object 1 reflections and/or diffractions of the ultrasound occur. The final result gives the positions of the above-mentioned virtual sources. In the case that a weld of a pipeline is examined in this manner, information can be obtained about the position, shape and magnitude of a possible defect. This is because a defect forms a virtual source and accordingly a collection of virtual point sources whose positions are determined by the position, shape and magnitude of the defect. So, this information in effect forms a three-dimensional picture of the material examined. Further, information can be obtained about the nature of the defect. For instance, of a weld of a pipeline comprising a cavity and accordingly a defect, it can be determined whether the cavity is filled with air, liquid or copper.

On the basis of the receiving signals the time can be mathematically inverted. With the wave theory, the detected wave field is traced back to the position where it came from, namely the position of the virtual sources. In this example, these virtual sources may, for instance, be welding defects. The wave theory takes into account both the amplitude and the delay time of the signal. The process of tracing back the measured wave field is called inverse wave field extrapolation and is known per se. Please note that the present invention is not restricted to the use of inverse wave field extrapolation but that also other techniques can be used within the system and method according to the invention.

If the signals of the unidimensional array of receivers were only processed when the receivers are each at one single position, a reasonable resolution in axial direction would be obtained. In axial direction, the unidimensional array in effect functions as a lens which makes a "sharp" picture in axial direction. However, in radial direction, the resolution is relatively poor. By also processing receiving signals from ultrasound receivers displaced relative to each other in radial direction, the resolution in radial direction can be improved. Then, the "effect of a lens" is also present in that direction. The result is that, with the signal-processing means, magnitude, position and even the shape of a virtual source and accordingly the magnitude, position, shape and nature of, for instance, defects in the weld of the object 1 can be detected. More in general, the position, shape, magnitude and nature of "irregularities" in the interior material can be determined. This can for example be realized by moving the unidimensional array of ultrasound receivers 16.*i* around the pipeline using the moving means. The speed of the movement may for instance be such that, between the transmissions of two ultrasound pulses, the linear array is moved over a distance equal to the distance between adjacent ultrasound receivers of the linear array. More particular, the speed of the movement may for instance be such that, between the series of transmissions of ultrasound pulses for (a significant part of) all individual transmitters, the linear array is moved over a distance small enough not to influence the resulting picture of each series substantially. However, other, for instance smaller, distances are also possible. One possibility is a distance of a few millimeters. All this means that, in this example, when the linear array has been moved over a predetermined distance, again ultrasound is supplied to the interior of the body of the object 1. Completely analogously, using each of the ultrasound receivers 16.*i*, a receiving signal is generated which is supplied to the respective signal-processing units 22.*i*. So, the ultrasound receivers are acoustically coupled to the outer surface of the object at positions which are, in this example at different times, distributed in two dimensions of the surface of the object for generating receiving signals. That, in this example, the respective positions are distributed in two dimensions of the surface of the object at different times and not at one point in time, is, on the one hand, the result of the receivers 16.*i* being arranged relative to each other according to a unidimensional array and, on the other hand, the result of the receivers being moved as discussed hereinabove. Were the receivers 16.*i* not moved, then the respective positions would be distributed in one dimension of the surface not only at one point in time but at different times. In an alternative embodiment, not shown, the ultrasound receivers can be arranged relative to each other according to a two or three dimensional array.

The final result of processing the receiving signals is in accordance with the present embodiment obtained as follows. The signal-processing units 22.*i* of a modular unit A, B, C, D are arranged for processing the respective receiving signals separately and in parallel into respective separate pixel values, which are optionally (at least temporarily) stored in the respective memories 25.*i*. The signal-processing units 22.*i* belonging to one modular unit A, B, C, D are arranged for combining the separate pixel values of all the ultrasound receivers of the respective group of ultrasound receivers to a sub-image which is (at least temporarily) stored in a respective memory 29.A, 29.B, 29.C, 29.D of the modular unit. The combination is in this embodiment effected in the memory 29.A, 29.B, 29.C, 29D itself, but can in an alternative embodiment be performed by a separate summing device.

Each modular unit A, B, C, D is connectable by connection means 24, 26, 28 (in this case point-to-point connections) to one or two other modular units, wherein the connection means 24, 26, 28 enable data communication between connected modular units such that the stored sub-images can be exchanged between connected modular units. The signal-processing means are arranged such that e.g. under control of the communication and control unit 27 the sub-image stored in the memory 29.A of modular unit A is transmitted by the connection means 24 to modular unit B where it is combined with the sub-image stored in the memory 29.B of the modular unit B to a combined sub-image. This combined sub-image is temporarily stored in the memory 29.B (at which time for instance the previously stored sub-image is deleted or which combined sub-image is stored in addition to the sub-image in the memory or in an alternative embodiment the combined sub-image is stored in a further memory of modular unit B) at least until it is further processed. This further processing in this example is that the combined sub-image stored in modular unit B is sent via the connection means 26 to modular unit C in which it is combined with a the sub-image stored in the memory 29.C of modular unit C, and the combined sub-image in which three sub-images are combined is at least temporarily stored in the memory 29.C of modular unit C. Finally the three combined sub-images stored in the memory 29.C as a combined sub-image is transmitted via the connection means 28 to modular unit D in which it is combined with the sub-image stored in the memory 29.D of modular unit D to the first image originating from the transmission of the first ultrasound signal. This first image can be stored in memory 29.D but is also transmitted via a transmission line 30 to the communication and control unit 27, where it optionally after it has been processed into a picture can be displayed on a display 31 and stored in a memory 32.

The same processing is performed for the second and all further ultrasound signals, and the first, second and all further signals are stored in the memory 32 of the communication and control unit 27. In the present example the first, second and all further images are combined (by the memory or a separate combiner) with each other and said combination is stored in the memory 32, however, in an alternative embodiment the signals can be stored separately. In a further alternative embodiment each first, second and further image can be transmitted (separately or combined) by a communication unit 33 of the communication and control unit 27 for further processing, e.g. to a remote system controller for converting the images into pictures, which can sent results of the further processing back to the communication and control unit for display on the display 31.

In an alternative embodiment the modular units and the signal-processing units of the modular units are controlled such as for combining a sub-image originating from the further ultrasound signal with a previous image to a combined hybrid image, for storing said combined hybrid image in a further memory at least until it is further processed by combining said combined hybrid image with a further sub-image originating from the further ultrasound signal, different from an already processed sub-image originating from the further ultrasound signal, and for at least temporarily storing the combination of all sub-images originating from the further ultrasound signal with the previous image. This is made possible by the connection means 24, 26, 28, 30 which allow a (previous) image (originating from a previous ultrasound signal) to be transmitted to a modular unit in which a sub-image originating from further ultrasound signal is stored. Please note that previous here relates to the order in which the images are processed.

In this example, the receiving signals are processed in real time. Now the position, magnitude, shape and nature of each virtual source are known, the information obtained about the virtual sources can be imaged on the display in various manners. For instance an, in perspective, three-dimensional picture of the interior material can be made. Here, one looks through the object from outside, as it were. However, it is also possible to have the point of view from which the material is imaged inside the material. The point of view and the direction of view may then be chosen by an operator, for instance using a joystick. One travels through the material, looking around, as it were. Such variants are understood to be within the framework of the invention.

Due to the modular construction and the point-to-point connections the number of ultrasound receivers can be easily extended by adding additional groups of, in this example, 32 ultrasound receivers with their modular unit to the already present modular units.

In the embodiment described above the combination of the sub-images takes place in the order A, B, C, D, however, in alternative embodiments this order can differ.

In the embodiment described above a sub-image is combined with another sub-image to a combined sub-image, which combined sub-image is combined with a further sub-image etc. However, in an alternative embodiment the sub-images can be separately transmitted to the communication and control unit 27 where they are combined to the first image.

In the embodiment described above each of the signal-processing units of one modular unit provides its respective separate pixel value to the memory 25.*i* of said modular unit where the separate pixel values are combined to a sub-image. However, in an alternative embodiment (not shown) the signal-processing units 22.*i* of one modular unit are arranged (and controlled by the communication and control unit 27) for:

a) processing by one of the signal-processing units 22.*i* one of the receiving signals generated by one of the ultrasound receivers 16.*i* into a separate pixel value, and storing said separate pixel value at least temporarily in the memory 25.*i* of said one of the signal-processing units, b) processing by another one of the signal-processing units another one of the receiving signals generated by another one of the ultrasound receivers, different from said one of the ultrasound receivers, separately into another separate pixel value, and storing said another separate pixel value at least temporarily in the memory of said another one of the signal-processing units, c) combining said another separate pixel value with the separate pixel value into a combined pixel value, and storing said combined pixel value in a further memory of the signal-processing means, d) processing by a further one of the signal-processing units a further one of the receiving signals generated by a further one of the ultrasound receivers, different from the ultrasound receivers of which the receiving signals have already been processed, separately into a further separate pixel value, and storing said further separate pixel value at least temporarily in the memory of said further one of the signal-processing units, e) combining said further separate pixel value with the stored combined pixel value into a further combined pixel value, and for replacing said stored combined pixel value in said further memory by said further combined pixel value, and f) repeating steps d) and e) until the receiving signals generated by a plurality of, preferably all, of the second number of ultrasound receivers are processed, and g) at least temporarily storing the combined pixel values of said plurality of, preferably all, the second number of ultrasound receivers as the first image in said further memory. To realize this each of the signal-processing units is connected by connection means to one or two other signal-processing units of the same modular unit, said connection means enabling communication of data between the memories of the signal-processing units. In this alternative embodiment the order in which the separate pixel values are combined can be any desired order. Although in the embodiments described above modular units comprising a number of ultrasound receivers are used, in alternative embodiments the ultrasound receivers can be separately organized, i.e. not combined to groups. In the present case this means that there are 128 separate signal-processing units each of which is connected by connection means to one or two other signal-processing units, said connection means enabling communication of data between the memories of the signal-processing units, so that the separate pixel values can be combined as described above. In a further alternative embodiment the 128 separate signal-processing means can each be connected by a connection means to the communication and control unit 27 where the separate pixel values are combined to the first or second or further image.

Thus in accordance with the embodiment of the invention as described above the received signals are processed in parallel and (in several alternative ways) combined into information of individual pixels of the combined first image.

Please note that in the present example the contents of a memory are deleted after this content has been further processed, but that in alternative embodiments this content can be stored for a prolonged time period.

It is noted that, for each of the embodiments described hereinabove, it holds true that the sound can be transmitted in the form of transversal waves and/or compression waves as desired. In the case that the object to be examined is a metal object, generally either transversal waves or compression waves will be used. In the case that the object is a human body, preferably, use will only be made of compression waves because precisely compression waves can propagate well in the body due to the properties of the human body.

The invention claimed is:

1. A method for examining the interior material of an object from a surface of an object using ultrasound having a frequency of at least 100 kHz, wherein the method comprises:

transmitting at least a first ultrasound signal by a first ultrasound transmitter of a first number of ultrasound transmitters to the interior material of the object, for forming a first image, in order to determine where reflections and/or diffractions occur in the interior material of the object, receiving reflections and/or diffractions of the first ultrasound signal from the interior material of the object using a second number of ultrasound receivers which are acoustically coupled to the surface of the object at positions which are distributed in at least one dimension of the surface of the object, generating, with each of the second number of ultrasound receivers, a receiving signal is generated from the received reflections and/or diffractions of the first ultrasound signal from the interior material of the object, separately processing each respective receiving signal generated by each of the second number of ultrasound receivers, and combining the separately processed receiving signals of a plurality of the second number of ultrasound receivers to form the first image, wherein the separately processing each respective receiving signal comprises:

a) converting the receiving signal into a separate dataset in a certain data format; and b) using the separate dataset in forming the first image;

wherein, during the separately processing, two or more of the receiving signals generated by two or more of ultrasound receivers are separately processed in parallel, wherein the second number of ultrasound receivers comprises individual groups of ultrasound receivers, each individual group having a third number of ultrasound receivers, wherein the method further comprises forming sub-images by combining the separate datasets of all the ultrasound receivers of one group of ultrasound receivers to form each one of the sub-images, the receiving signals generated by all the ultrasound receivers of one group of ultrasound receivers being separately processed in parallel during the separately processing, wherein each of the sub-images is temporarily stored in a memory at least until it is further processed, wherein the number of groups of the second number of ultrasound receivers is at least three, wherein the method further comprises combining a sub-image with another sub-image of the sub-images to form a combined sub-image, the combined sub-image being temporarily stored in a memory at least until it is further processed by combining said combined sub-image with a further sub-image, different from already processed sub-images, and wherein the combination of all sub-images is the first image which first image is at least temporarily stored, wherein a sub-image originating from a further ultrasound signal is combined with a previous image originating from a previous ultrasound signal to form a combined hybrid image, the combined hybrid image being temporarily stored in a memory at least until it is further processed by combining the combined hybrid image with a further sub-image originating from the further ultrasound signal, the further sub-image being different from an already processed sub-image originating from the further ultrasound signal, and wherein a combination of all sub-images originating from the further ultrasound signal with the previous image is at least temporarily stored.

2. The method according to claim 1, wherein each of the separate datasets is temporarily stored at least until the separate datasets of said plurality of the second number of ultrasound receivers have been obtained, after which all the separate datasets are combined to the first image, which first image is at least temporarily stored.

3. The method according to claim 2, wherein after the first image has been stored all stored separate datasets are deleted.

4. The method according to claim 1, wherein the method comprises:
   a) processing one of the receiving signals generated by one of the ultrasound receivers into a separate dataset, and storing said separate dataset at least temporarily in a memory,
   b) processing another one of the receiving signals generated by another one of the ultrasound receivers, different from said one of the ultrasound receivers, separately into a another separate dataset, combining said another separate dataset with the stored separate dataset into a combined dataset, and replacing said stored separate dataset in said memory by said combined dataset,
   c) processing a further one of the receiving signals generated by a further one of the ultrasound receivers, different from the ultrasound receivers of which the receiving signals have already been processed, separately into a further separate dataset, combining said further separate dataset with the stored combined dataset into a further combined dataset, and replacing said stored combined dataset in said memory by said further combined dataset, and
   d) repeating step c) until the receiving signals generated by said plurality of the second number of ultrasound receivers are processed, and wherein the combined dataset of said plurality of the second number of ultrasound receivers is the first image which is at least temporarily stored.

5. The method according to claim 1, wherein the second number of ultrasound receivers is distributed in an array extending in one dimension of the surface of the object.

6. The method according to claim 1, wherein the ultrasound receivers are arranged relative to each other according to a two or three-dimensional array.

7. The method according to claim 1, wherein the method comprises the further step of transmitting at least a further ultrasound signal by a further ultrasound transmitter of said first number of ultrasounds transmitters to the interior material of the object for forming a further image in the same way as the first image, said further ultrasound transmitter being different from the first ultrasound transmitter.

8. The method according to claim 7, wherein the first ultrasound signal and at least one further ultrasound signal are transmitted simultaneously.

9. The method according to claim 7, wherein the first and the further image are combined and the combined image is stored in the memory.

10. The method according to claim 9, wherein after the combined image has been stored in the memory, the first and/or the further image are deleted.

11. The method according to claim 9, wherein the combined image of the images originating from all the ultrasound transmitters of the first number of ultrasound transmitters is transmitted for further processing.

12. The method according to 7, wherein the first and further images are transmitted separately for further processing.

13. The method according to claim 1, wherein the ultrasound transmitters also form the ultrasound receivers, the first number being equal to the second number.

14. The method according to claim 1, wherein the ultrasound transmitters are separate from the ultrasound receivers.

15. The method according to claim 1, wherein the receiving signals are processed in real time.

16. The method according to claim 1, wherein a weld of a metal, plastic or composite pipeline is examined.

17. The method according to claim 1, wherein a wall of a metal, plastic or composite pipeline or a metal, plastic or composite sheet is examined.

18. The method according to claim 1, wherein a human body is examined.

19. The method according to claim 1, wherein a dataset is in the form of a data point, a picture, a picture element or pixel or a pixel value.

20. The method according to claim 1, wherein the data format is chosen such that addition or combination of datasets is facilitated.

21. A system for examining the interior material of an object from a surface of an object using ultrasound having a frequency of at least 100 kHz, wherein the system comprises:
   a first ultrasound transmitter of a first number of ultrasound transmitters for supplying ultrasound to the interior material of the object,
   a second number of ultrasound receivers which are acoustically coupled to the surface of the object at positions which are distributed in at least one dimension of the surface of the object, for receiving reflections and/or diffractions of the ultrasound from the interior material of the object, and
   a signal processor configured to process receiving signals coming from the respective ultrasound receivers, wherein, during use, a receiving signal is generated with each of the ultrasound receivers, wherein the signal processor is arranged to process the receiving signals from the ultrasound receivers, for forming a first image, in order to determine where reflections and/or diffractions of the ultrasound occur in the interior material of the object,
   wherein the signal processor is arranged for carrying out a method for processing receiving signals coming from the ultrasound receivers separately, and for combining the separately processed receiving signals of a plurality of the ultrasound receivers to form the first image,
   wherein during processing each receiving signal, the method includes:
   a) converting the receiving signal into a separate dataset in a data format; and
   b) using the separate dataset in forming the first image,
   wherein a set of signal processing units of the signal processor is arranged for processing the respective receiving signals in parallel, and
   wherein the second number of ultrasound receivers comprises individual groups of ultrasound receivers, each individual group having a third number of ultrasound receivers,
   wherein ones of the signal-processing units, which are associated with ones of the ultrasound receivers of each group of the individual groups of ultrasound receivers, are combined into a modular unit for forming sub-images, the signal-processing units of the modular unit being arranged for combining the separate datasets of all the ultrasound receivers of one group of ultrasound receivers to form a sub-image of the sub-images, wherein the modular unit is arranged for temporarily storing a sub-image in a memory of the system at least until it is further processed, wherein the signal processor is arranged for combining a sub-image stored in one modular unit with another sub-image stored in another modular unit to form a combined sub-image using two of the sub-images, and for temporarily storing the combined sub-image in a memory of the system at least until it is further processed by combining the combined sub-image with a further sub-image, different from the already processed sub-image with a further sub-image, different from the already processed sub-images, stored in a further modular unit, and for at least temporarily storing the combination of all sub-images as the first image, and wherein the signal processor is arranged for:

combining a sub-image originating from a further ultrasound signal with a previous image originating from a previous ultrasound signal to form a combined hybrid image, storing said combined hybrid image in a further memory at least until it is further processed by combing said combined hybrid image with a further sub-image originating from the further ultrasound signal, the further sub-image being different from an already processed sub-image originating from the further ultrasound signal, and at least temporarily storing the combination of all sub-images originating from the further ultrasound signal with the previous image.

22. The system according to claim 21, wherein the signal processor comprises a number of the signal-processing units, said number being equal to the second number, wherein each signal-processing unit comprises an acquisition input for acquiring a receiving signal coming from a respective ultrasound receiver, a receiving signal processor for processing said receiving signal from the respective ultrasound receiver and optionally a memory for at least temporarily storing a respective separate dataset.

23. The system according to claim 22, wherein the signal-processing units are arranged for storing each of the separate datasets temporarily at least until the separate datasets of said plurality of the second number of ultrasound receivers have been obtained, for thereafter combining all the separate datasets to the first image, and for at least temporarily storing said first image.

24. The system according to claim 23, wherein the signal-processing units are arranged for deleting all stored separate datasets after storing the first image.

25. The system according to claim 22, wherein the signal processor signal processor is arranged for:

a) processing by one of the signal-processing units one of the receiving signals generated by one of the ultrasound receivers into a separate dataset, and storing said separate dataset at least temporarily in the memory of said one of the signal-processing units, b) processing by another one of the signal-processing units another one of the receiving signals generated by another one of the ultrasound receivers, different from said one of the ultrasound receivers, separately into another separate dataset, and storing said another separate dataset at least temporarily in the memory of said another one of the signal-processing units, c) combining said another separate dataset with the separate dataset into a combined dataset, and storing said combined dataset in a further memory of the signal-processing means, d) processing by a further one of the signal-processing units a further one of the receiving signals generated by a further one of the ultrasound receivers, different from the ultrasound receivers of which the receiving signals have already been processed, separately into a further separate dataset, and storing said further separate dataset at least temporarily in the memory of said further one of the signal-processing units, e) combining said further separate dataset with the stored combined dataset into a further combined dataset, and for replacing said stored combined dataset in said further memory by said further combined dataset, f) repeating steps d) and e) until the receiving signals generated by said plurality of the second number of ultrasound receivers are processed, and g) at least temporarily storing the combined dataset of said plurality of the second number of ultrasound receivers as the first image in said further memory.

26. The system according to claim 21, wherein the second number of ultrasound receivers is distributed in an array extending in one dimension of the surface of the object.

27. The system according to claim 21, wherein the ultrasound receivers are arranged relative to each other according to a two or three dimensional array.

28. The system according to claim 21, wherein the system is further arranged for transmitting at least a further ultrasound signal by a further ultrasound transmitter of said first number of ultrasounds transmitters to the interior material of the object and for forming a further image in the same way as the first image, said further ultrasound transmitter being different from the first ultrasound transmitter.

29. The system according to claim 28, wherein the system is further arranged for transmitting said first ultrasound signal and at least one further ultrasound signal simultaneously.

30. The system according to claim 28, wherein the signal processor is arranged for combining the first and the further image and for storing the combined image in a further memory.

31. The system according to claim 29, wherein the signal processor is arranged for deleting the first and/or the further image after the combined image has been stored in said further memory.

32. The system according to claim 28, wherein the system comprises a communication unit and wherein the signal processor is arranged for passing through the first and further images separately to the communication unit for further processing.

33. The system according to claim 21, wherein each of the signal-processing units is connected to one or two other signal-processing units, thereby enabling communication of data between the memories of the signal-processing units.

34. The system according to claim 33, wherein the connections are point-to-point connections.

35. The system according to claim 21, wherein each modular unit is connectable to one or two other modular units, thereby enabling data communication between connected modular units.

36. The system according to claim 21, wherein the system comprises a communication unit and wherein the signal processor is arranged for passing through the combined image of the datasets originating from all the ultrasound transmitters of the first number of ultrasound transmitters to the communication unit for transmitting said combined image for further processing.

37. The system according to claim 21, wherein the ultrasound transmitters also form the ultrasound receivers, the first number being equal to the second number.

38. The system according to claim 21, wherein the ultrasound transmitters are separate from the ultrasound receivers.

39. The system according to claim 21, wherein the signal processor is arranged for processing the receiving signals in real time.

40. The system according to claim 21, wherein the system is arranged for examining a weld of a metal, plastic or composite pipeline or a wall of a metal, plastic or composite pipeline or a human body.

41. The system according to claim 21, wherein the signal processor is arranged for converting the receiving signal into a separate dataset in a data format, said separate dataset being a data point, a picture, a picture element or pixel or a pixel value.

42. The system according to claim 41, wherein the signal processor is arranged for converting the receiving signal into a separate dataset in a data format, said data format being such that addition or combination of datasets is facilitated.

* * * * *